(12) United States Patent
Lai et al.

(10) Patent No.: US 7,482,416 B2
(45) Date of Patent: Jan. 27, 2009

(54) PREPOLYMERS FOR IMPROVED SURFACE MODIFICATION OF CONTACT LENSES

(75) Inventors: Yu-Chin Lai, Pittsford, NY (US); Edmond T. Quinn, Rochester, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 0 days.

(21) Appl. No.: 11/955,683

(22) Filed: Dec. 13, 2007

(65) Prior Publication Data

US 2008/0097002 A1 Apr. 24, 2008

Related U.S. Application Data

(62) Division of application No. 10/876,969, filed on Jun. 25, 2004, now abandoned.

(51) Int. Cl.
*C08F 130/08* (2006.01)
(52) U.S. Cl. .................... 526/279; 528/32; 523/107
(58) Field of Classification Search ............. 526/279; 528/32; 523/107
See application file for complete search history.

(56) References Cited

U.S. PATENT DOCUMENTS

| | | |
|---|---|---|
| 3,408,429 A | 10/1968 | Wichterle |
| 3,496,254 A | 2/1970 | Wichterle |
| 4,084,459 A | 4/1978 | Clark |
| 4,136,250 A | 1/1979 | Mueller et al. |
| 4,153,641 A | 5/1979 | Deichert et al. |
| 4,192,827 A | 3/1980 | Mueller et al. |
| 4,197,266 A | 4/1980 | Clark et al. |
| 4,486,577 A | 12/1984 | Mueller et al. |
| 4,605,712 A | 8/1986 | Mueller et al. |
| 4,740,533 A | 4/1988 | Su et al. |
| 4,910,277 A | 3/1990 | Bambury et al. |
| 4,954,587 A | 9/1990 | Mueller |
| 5,034,461 A | 7/1991 | Lai et al. |
| 5,070,215 A | 12/1991 | Bambury et al. |
| 5,260,000 A | 11/1993 | Nandu et al. |
| 5,271,875 A | 12/1993 | Appleton et al. |
| 5,310,779 A | 5/1994 | Lai |
| 5,358,995 A | 10/1994 | Lai et al. |
| 5,374,662 A | 12/1994 | Lai et al. |
| 5,420,324 A | 5/1995 | Lai et al. |
| 5,496,871 A | 3/1996 | Lai et al. |
| 6,218,503 B1 | 4/2001 | Lai et al. |
| 6,268,467 B1 | 7/2001 | Lai et al. |
| 6,743,878 B2 | 6/2004 | Bowers et al. |
| 7,084,188 B2 | 8/2006 | Lai et al. |
| 7,176,268 B2 | 2/2007 | Lai et al. |
| 2002/0102415 A1 | 8/2002 | Valint et al. |

FOREIGN PATENT DOCUMENTS

| | | |
|---|---|---|
| JP | 05339377 | 12/1993 |
| JP | 2002 179796 | 6/2002 |
| WO | WO2005/056651 | 6/2005 |

*Primary Examiner*—Kuo-Liang Peng
(74) *Attorney, Agent, or Firm*—Glenn D. Smith

(57) ABSTRACT

Provided are a novel class of fumaric- and itaconic-containing prepolymers and compositions comprising the prepolymers used in the manufacture of medical devices.

46 Claims, No Drawings

PREPOLYMERS FOR IMPROVED SURFACE MODIFICATION OF CONTACT LENSES

This application is a divisional of U.S. application Ser. No. 10/876,969, filed on Jun. 25, 2004, now abandoned herein incorporated by reference.

FIELD OF THE INVENTION

The present invention relates generally to a novel class of fumaric- and itaconic-containing prepolymers and compositions comprising the prepolymers used in the manufacture of medical devices. More specifically, the present invention relates to fumaric- and itaconic-containing prepolymers having siloxane groups and hydrophilic groups derived from a reactive oligomer of hydrophilic monomers. The prepolymers are useful in making surface modified medical devices such as contact lenses.

BACKGROUND OF THE INVENTION

Medical devices such as ophthalmic lenses made from silicone-containing materials have been investigated for a number of years. Such materials can generally be sub-divided into two major classes, namely hydrogels and non-hydrogels. Non-hydrogels do not absorb appreciable amounts of water, whereas hydrogels can absorb and retain water in an equilibrium state. Hydrogels generally have water content between about 15 to about 80 weight percent. Regardless of their water content, both non-hydrogel and hydrogel silicone medical devices tend to have relatively hydrophobic, non-wettable surfaces that have a high affinity for lipids. This problem is of particular concern with contact lenses.

Fumarate- and fumaramide-containing monomers and compositions comprising the monomers have been developed to make highly oxygen permeable hydrogels which may be used to make biomedical devices including contact lenses. Examples of these fumarate- and fumaramide-containing monomers and compositions can be found in U.S. Pat. Nos. 5,374,662, 5,420,324, and 5,496,871, the contents of each being incorporated by reference herein. Because of the polar character of amide functionality, this class of monomer shows good compatibility with both hydrophobic monomers such as tris(trimethylsiloxy)silane (TRIS) and hydrophilic monomers such as N, N-dimethylacrylamide (DMA). These prior art prepolymers give silicone hydrogels with excellent oxygen permeability and mechanical properties. However, like other silicone hydrogels, they are not wettable enough to be useful as continuous wear lenses unless the surface is treated.

Surface structure and composition determine many of the physical properties and ultimate uses of solid materials. Characteristics such as wetting, friction, and adhesion or lubricity are largely influenced by surface characteristics. The alteration of surface characteristics is of special significance in biotechnical applications where biocompatibility is of particular concern. Therefore, those skilled in the art have long recognized the need for rendering the surface of contact lenses and other medical devices hydrophilic or more hydrophilic. Increasing the hydrophilicity of the contact-lens surface improves the wettability of the contact lenses with tear fluid in the eye. This in turn improves the wear comfort of the contact lenses. In the case of continuous-wear lenses, the surface is especially important. The surface of a continuous-wear lens must be designed not only for comfort, but to avoid adverse reactions such as corneal edema, inflammation, or lymphocyte infiltration. Improved methods have accordingly been sought for modifying the surfaces of contact lenses, particularly high-Dk (highly oxygen permeable) lenses designed for continuous (overnight) wear.

Various patents disclose the attachment of hydrophilic or otherwise biocompatible polymeric chains to the surface of a contact lens in order to render the lens more biocompatible. For example, U.S. Pat. Pub. No. US 2002/0102415 A1 teaches plasma treatment of a fumarate- or fumaramide-containing substrate followed by reaction with other polymers, such as DMA/VDMO copolymer. U.S. patent application Ser. Nos. 10/728,531 and 10/728,711 teach fumaric- and itaconic-containing prepolymers having reactive functionality provided by residues having at least one reactive functional group.

Although manufacturing steps such as plasma treatment provide lenses having suitable coatings, it would be desirable to provide prepolymers having desirable surface activity to produce a surface treated lens without the need for plasma treatment or corona discharge treatment.

SUMMARY OF THE INVENTION

In accordance with the present invention, a novel class of fumaric- and itaconic-prepolymers with both siloxane and hydrophilic groups are disclosed for use with both silicone and non-silicone containing polymeric systems used for biomedical devices, especially contact lenses. The novel prepolymers have the following schematic representations:

and

wherein $R_1$ is an alkyl diradical that may have ether linkages, $R_2$ and $R_3$ are independently alkyl or phenyl groups, unsubstituted or substituted with halogen and ether linkages, W is O or NH, m is an integer between 2 and 200, and Y is a residue derived from a reactive oligomer of hydrophilic monomers. This reactive oligomer can be prepared by radical polymerization of a hydrophilic monomer/comonomer in an organic solution which also contains a quantitative amount of an amino or hydroxy-containing chain transfer agent so that the molecular weight of the oligomer can be maintained at a level suitable for making a prepolymer of this invention for a targeted application.

The invention is further directed toward hydrogels formed of a polymerizable mix comprising the novel class of fumaric- and itaconic-containing prepolymers with both siloxane and hydrophilic groups. Such hydrogels are useful in forming medical devices.

DETAILED DESCRIPTION OF THE INVENTION

As stated above, the present invention is directed toward a novel class of fumaric- and itaconic-containing prepolymers with both siloxane and hydrophilic groups, useful in copolymerizable polymeric systems used for biomedical devices, especially contact lenses. As used herein, fumaric refers to a derivative of fumaric acid and can be a fumarate (an ester), a fumaramide (an amide) or a residue having both ester and amide functionalities. The fumaric group is a residue of trans-1,2-ethylenedicarboxylate. Therefore, it will be understood that the diastereoisomer of fumarate, maleate, is also intended to be included in the fumaric-containing prepolymers of the present invention. Itaconic refers to derivatives of itaconic acid and has a similar meaning as that of fumaric. In further embodiments of the present invention, the novel prepolymers are used to make biomedical devices and are useful in contact lens formulations which may be either "soft" or "hard" and which may preferably be hydrogels.

As is known in the field, certain crosslinked polymeric materials may be polymerized to form a hard, water-free, xerogel. Xerogels are understood to be unhydrated hydrogel formulations. It was found that such xerogels could be physically altered to, for example, impart optical properties through machining, and then be hydrated and retain their water content.

When the term "polymerization" is used herein we refer to the polymerization of the double bonds of the monomers and prepolymers endcapped with polymerizable unsaturated groups which results in a crosslinked three-dimensional network.

Further, notations such as "(meth)acrylate" or "(meth)acrylamide" are used herein to denote optional methyl substitution. Thus, for example, (meth)acrylate includes both acrylate and methacrylate and N-alkyl-(meth)acrylamide includes both N-alkyl acrylamide and N-alkyl methacrylamide.

The term "prepolymer" denotes a high molecular weight monomer containing polymerizable groups. The monomers added to the monomeric mixture of the present invention may therefore be low molecular weight monomers or prepolymers. Thus, it is understood that a term such as "silicone-containing monomers" includes "silicone-containing prepolymers".

The terms "shaped articles for use in biomedical applications" or "biomedical devices or materials" or "biocompatible materials" mean the hydrogel materials disclosed herein have physicochemical properties rendering them suitable for prolonged contact with living tissue, blood and the mucous membranes.

While the present invention contemplates the use of a novel class of fumaric- and itaconic-containing prepolymers with both siloxane and hydrophilic groups for medical devices including both "hard" and "soft" contact lenses, the formulations containing the novel class of fumaric- and itaconic-containing prepolymers with both siloxane and hydrophilic groups of the present invention are thought to be especially useful as soft hydrogel contact lenses. As is understood in the field, a lens is considered to be "soft" if it can be folded back upon itself without breaking while in the fully hydrated state.

A hydrogel is a hydrated cross-linked polymeric system that contains water in an equilibrium state. Silicone hydrogels (i.e., hydrogels containing silicone) are usually prepared by polymerizing a mixture containing at least one silicone-containing monomer and at least one hydrophilic monomer. By the term silicone, it is meant that the material is an organic polymer comprising at least five percent by weight silicone (—OSi—linkages), preferably about 10 to about 95 percent by weight silicone, more preferably about 30 to about 90 percent by weight silicone. Applicable silicone-containing monomeric units for use in the formation of silicone hydrogels are well known in the art and numerous examples are provided in U.S. Pat. Nos. 4,136,250; 4,153,641; 4,740,533; 5,034,461; 5,070,215; 5,260,000; 5,310,779; and 5,358,995.

The novel classes of fumaric- and itaconic-containing prepolymers with both siloxane and hydrophilic groups of the present invention have at least one fumaric or itaconic group. Monomer mixes comprising the novel prepolymers of the present invention may comprise both thermal- and photo-initiators for curing purposes. The monomer mixes may further comprise at least one additional hydrophilic monomer. Further, the monomer mix may additionally comprise at least one silicone-containing monomer.

The fumaric- and itaconic-containing prepolymers of the present invention are prepared according to syntheses well known in the art and according to the examples disclosed herein. The novel class of fumaric- and itaconic-containing prepolymers with both siloxane and hydrophilic groups of the present invention are incorporated into the monomer mix. The relative weight % of the novel class of fumaric- and itaconic-containing prepolymers with both siloxane and hydrophilic groups as compared to the total monomer mix weight % is from about 10% to about 80%, more preferably from about 10% to about 50%, and most preferably about 15% to about 40%.

Examples of hydrophilic monomers include, but are not limited to, amide, hydroxy or zwifterionic containing hydrophilic monomers such as ethylenically unsaturated lactam-containing monomers including N-vinyl pyrrolidinone; methacrylic and acrylic acids; (meth)acrylic substituted alcohols, such as 2-hydroxyethylmethacrylate (HEMA), 2-hydroxyethylacrylate, glycerol methacrylate and polyethyleneglycol monomethacrylate; and (meth)acrylamides, such as methacrylamide and N,N-dimethylacrylamide (DMA); vinyl carbonate or vinyl carbamate monomers such as disclosed in U.S. Pat. No. 5,070,215, the contents of which are incorporated herein by reference; oxazolinone monomers such as disclosed in U.S. Pat. No. 4,910,277, the contents of which are incorporated herein by reference and hydrophilic zwitterionic monomers such as disclosed in U.S. Pat. No. 6,743,878, the contents of which are incorporated herein by reference.

Preferred hydrophilic vinyl-containing monomers that may be incorporated into the hydrogels of the present invention include monomers such as N-vinyl lactams such as N-vinyl pyrrolidinone (NVP), N-vinyl-N-methyl acetamide, N-vinyl-N-ethyl acetamide, N-vinyl-N-ethyl formamide, N-vinyl formamide, with NVP being the most preferred.

Preferred hydrophilic acrylic-containing monomers which may be incorporated into the hydrogel of the present invention include hydrophilic monomers such as N,N-dimethyl acrylamide (DMA), 2-hydroxyethyl methacrylate, glycerol methacrylate, 2-hydroxyethyl methacrylamide, methacrylic acid and acrylic acid, with DMA being the most preferred. Other suitable hydrophilic monomers will be apparent to one skilled in the art. The relative weight % of hydrophilic monomer(s) to total weight % of the comonomer mix is preferably from about 5% to about 80%, more preferably from about 20% to about 70%, and most preferably about 20% to about 40%.

As mentioned previously, additional silicone-containing monomers may be present in the monomer mixes with the novel class of fumaric- or itaconic-containing monomers. One preferred class of suitable silicone-containing monomers which may be incorporated into a monomer mix with the novel class of fumaric- and itaconic-containing prepolymers with both siloxane and hydrophilic groups of the present invention are the bulky polysiloxanylalkyl (meth)acrylic monomers represented by the following Formula (I):

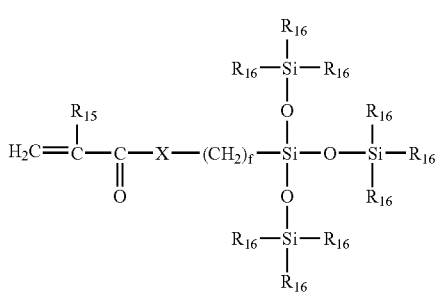

wherein: X is O or NR; each $R_{15}$ is independently hydrogen or an alkyl group having 1 to 10 carbon atoms; and each $R_{16}$ is independently a lower alkyl or phenyl group; and f is 1 or 3 to 10.

Such bulky monomers include methacryloxypropyl tris (trimethylsiloxy)silane(TRIS), pentamethyldisiloxanylmethylmethacrylate, tris(trimethylsiloxy)methacryloxy propylsilane, phenyltetramethyldisiloxanylethyl acrylate, and methyldi(trimethylsiloxy)methacryloxymethyl silane. Further preferred classes of silicone-containing monomers which may be incorporated into a monomer mix with the reactive functionalized fumaric- or itaconic-containing monomers of the present invention are the poly(organosiloxane) monomers represented by the following formula (II):

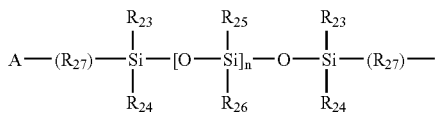

wherein: A is an activated unsaturated group, such as an ester or amide of an acrylic or a methacrylic acid; each $R_{23}$-$R_{26}$ is independently selected from the group consisting of a monovalent hydrocarbon radical or a halogen substituted monovalent hydrocarbon radical having 1 to 18 carbon atoms which may have ether linkages between carbon atoms; $R_{27}$ is a divalent hydrocarbon radical having from 1 to 22 carbon atoms; and n is 0 or an integer greater than or equal to 1. When siloxane-containing monomers, other than our novel silicone containing prepolymers, are incorporated into the monomer mix, the weight % of the other siloxane-containing monomers as compared to the total monomer mix weight % is from about 5% to about 60%, more preferably from about 10% to about 50%, and most preferably about 10% to about 40%.

Either the silicone-containing monomer, the novel class of fumaric- or itaconic-containing prepolymers with both siloxane and hydrophilic groups, or the hydrophilic monomer may function as a crosslinking agent (a crosslinker), the crosslinking agent being defined as a monomer having multiple polymerizable functionalities. Additional crosslinkers also may be present in the monomer mix which polymerizes to form the hydrogel.

Many commonly used crosslinking agents are hydrophobic. When it is desirable for both an acrylic-containing monomer and a vinyl-containing monomer to be incorporated into the silicone-containing polymer of the present invention, because these vinyl- and acrylic-containing monomers have differing reactivity ratios and may not copolymerize efficiently, a further crosslinking agent having both a vinyl and an acrylic polymerizable group may be used. Such crosslinkers which facilitate the copolymerization of these monomers are the subject of U.S. Pat. No. 5,310,779, the content of which is incorporated herein by reference.

Such crosslinkers are represented by the following schematic representation:

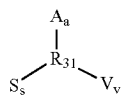

wherein V denotes a vinyl-containing group having the formula:

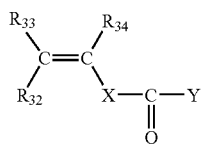

A denotes an acrylic-containing group having the formula:

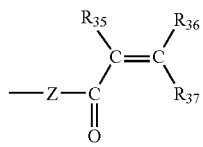

S denotes a styrene-containing group having the formula:

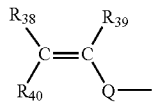

wherein $R_{31}$ is an alkyl radical derived from substituted and unsubstituted hydrocarbons, polyalkylene oxide, poly(perfluoro) alkylene oxide, dialkyl-capped polydimethylsiloxane, dialkyl-capped polydimethylsiloxane modified with fluoroalkyl or fluoroether groups; $R_{32}$-$R_{40}$ are independently H, or alkyl of 1 to 5 carbon atoms; Q is an organic group containing aromatic moieties having 6-30 carbon atoms; X, Y, and Z are independently O, NH or S; v is 1, or higher; and a, are independently greater than or equal to 0; and a+s is greater than or equal to 1. An example is 2-hydroxyethylmethacrylate vinyl carbonate or carbamate.

Other crosslinking agents which may be incorporated into the silicone-containing hydrogel of the present invention include polyvinyl, typically di- or tri-vinyl monomers, most commonly the di- or tri(meth)acrylates of dihydric ethylene glycol, triethylene glycol, butylene glycol, hexane-1,6-diol, thio-diethylene glycol-diacrylate and methacrylate; neopentyl glycol diacrylate; trimethylolpropane triacrylate and the like; N,N'-dihydroxyethylene-bisacrylamide and -bismethacrylamides; also diallyl compounds like diallyl phthalate and triallyl cyanurate; divinylbenzene; ethylene glycol divinyl ether; and the (meth)acrylate esters of polyols such as triethanolamine, glycerol, pentaerythritol, butylene glycol, mannitol, and sorbitol. Further examples include N,N-methylene-bis-(meth)acrylamide, sulfonated divinylbenzene, and divinylsulfone. Also useful are the reaction products of hydroxyalkyl (meth)acrylates with unsaturated isocyanates, for example the reaction product of 2-hydroxyethyl methacrylate with 2-isocyanatoethyl methacrylate (IEM). See U.S. Pat. No. 4,954,587.

Other known crosslinking agents are polyether-bisurethane-dimethacrylates (see U.S. Pat. No. 4,192,827), and those crosslinkers obtained by reaction of polyethylene glycol, polypropylene glycol and polytetramethylene glycol with 2-isocyanatoethyl methacrylate (IEM) or m-isopropenyl-γ, γ-dimethylbenzyl isocyanates (m-TMI), and polysiloxane-bisurethane-dimethacrylates. See U.S. Pat. Nos. 4,486,577 and 4,605,712. Still other known crosslinking agents are the reaction products of polyvinyl alcohol, ethoxylated polyvinyl alcohol or of polyvinyl alcohol-co-ethylene with 0.1 to 10 mol % vinyl isocyanates like IEM or m-TMI.

The prepolymers of the present invention, when copolymerized, are readily cured to cast shapes by methods such as UV polymerization, use of free radical thermal initiators and heat, or combinations thereof. Representative free radical thermal polymerization initiators are organic peroxides, such as for example acetyl peroxide, lauroyl peroxide, decanoyl peroxide, stearoyl peroxide, benzoyl peroxide, tertiary butyl peroxypivalate, peroxydicarbonate, and the commercially available thermal initiators such as LUPERSOL® 256, 225 (Atofina Chemicals, Philadelphia, Pa.) and the like, employed in a concentration of about 0.01 to about 2% by weight of the total monomer mixture. Representative UV initiators are those known in the field such as, benzoin methyl ether, benzoin ethyl ether, DAROCUR®-1173, 1164, 2273, 1116, 2959, 3331, IGRACURE® 651 and 184 (Ciba Specialty Chemicals, Ardsley, N.Y.).

In addition to the above-mentioned polymerization initiators, the copolymer of the present invention may also include other components as will be apparent to one skilled in the art. For example, the monomer mix may include additional colorants, or UV-absorbing agents and toughening agents such as those known in the contact lens art.

The resulting copolymers of this invention can be formed into contact lenses by the spincasting processes such as those disclosed in U.S. Pat. Nos. 3,408,429 and 3,496,254, static casting processes such as in U.S. Pat. No. 5,271,875 and other conventional methods, such as compression molding as disclosed in U.S. Pat. Nos. 4,084,459 and 4,197,266.

Polymerization of the monomer mix may be conducted either in a spinning mold, or a stationary mold corresponding to a desired contact lens shape. The thus-obtained contact lens may be further subjected to a mechanical finishing, as occasion demands. Also, the polymerization may be conducted in an appropriate mold or vessel to give a lens material in the form of button, plate or rod, which may then be processed (e.g., cut or polished via lathe or laser) to give a contact lens having a desired shape.

The hydrogels produced by the present invention are oxygen transporting, hydrolytically stable, biologically inert, and transparent. The monomers and prepolymers employed in accordance with this invention are readily polymerized to form three-dimensional networks which permit the transport of oxygen and are optically clear, strong and hydrophilic.

The present invention provides materials which can be usefully employed for the fabrication of prostheses such as heart valves and intraocular lenses, as optical contact lenses or as films. More particularly, the present invention concerns contact lenses.

The present invention further provides articles of manufacture which can be used for biomedical devices, such as, surgical devices, controlled drug delivery devices, heart valves, vessel substitutes, intrauterine devices, membranes and other films, diaphragms, surgical implants, blood vessels, artificial ureters, artificial breast tissue and membranes intended to come into contact with body fluid outside of the body, e.g., membranes for kidney dialysis and heart/lung machines and the like, catheters, mouth guards, denture liners, intraocular devices and especially contact lenses.

It is known that blood, for example, is readily and rapidly damaged when it comes into contact with artificial surfaces. The design of a synthetic surface which is antithrombogenic and nonhemolytic to blood is necessary for prostheses and devices used with blood.

Although the teachings of the present invention are preferably applied to soft or foldable contact lenses or like medical devices formed of a foldable or compressible material, the same may also be applied to harder, less flexible, materials such as lenses formed of a relatively rigid material such as poly(methyl methacrylate) (PMMA).

In one embodiment of the present invention, the novel class of fumaric- and itaconic-containing prepolymers with both siloxane and hydrophilic groups are used to produce a contact lens.

The novel class of fumaric- and itaconic-containing prepolymers with both siloxane and hydrophilic groups useful in certain embodiments of the present invention may be prepared according to syntheses well known in the art and according to the methods disclosed in the following examples.

EXAMPLES

Example 1

Preparation of Reactive Oligomer Derived from N-vinylpyrrolidone

To a thoroughly dried 1000-mL round bottom flask equipped with a reflux condenser, Nitrogen inlet, was charged with N-vinylpyrrolidone (100 g, 0.8997 mole), 2-mercaptoethanol (12.6 mL, 0.1796 mole), 400 mL anhydrous tetrahydrofuran and Vazo-64 (1.14 gram). The contents, while stirred at room temperature, were bubbled with nitrogen for about 15 minutes. The contents were then heated to reflux for 48 hours. NMR indicated some vinyl groups remaining. Then 0.5 grams of Vazo-64 was added and the contents were continued to be heated to reflux for an additional 4 days. Only a trace amount of vinyl groups remained. The solution was then condensed to 120 mL and then poured into 1200 mL of ether to precipitate the product. The product was dissolved/precipitated twice. The final product was a white powder.

The molecular weight of the oligomer product was determined by acid-base titration. It was first allowed to react with an excess amount of phenyl isocyanate, then with excess amount of dibutylamine, both in THF, followed by titrating with standardized 0.1 N hydrochloric acid. The molecular weight as determined was 416. (Theoretical 623)

Example 2

Preparation of α,ω-bi-hydroxybutyl-terminated polydimethylsiloxane (Mn 1376)

A 100-mL 4-neck round bottom flask was charged with 1,3-bis-hydroxybutyltetramethyldisiloxane (76.8 g, 0.273 mole), dimethoxyethyldimethylsilane (542 g, 4.51 moles). While mechanically stirring, through a dropping funnel, 297 mL conc. HCl and 81 grams (4.51 mole) of water was added into the flask over 30 minutes. The content of the flask (contents) was then heated with oil bath at 80° C. for one hour. The methanol was distilled off (total 318 mL of methanol collected over a period of 5 hours). Then, 159 mL of water and 15 mL of conc. HCl was added to the flask, the contents being refluxed at about 100-110° C. for 4 hours.

The content was cooled down and extracted with 300 mL of ether. The ether solution was extracted with 200 mL of water. After that, the ether solution was washed two times with 200 mL of 5% of Sodium bicarbonate aqueous solution, then three times with 200 mL of water each. The crude product was then dropped into a 25/75 by weight mix of methanol/water (712 grams) in a conical flask while mixed with a stirrer.

The mixture was poured into a separatory funnel. The bottom layer was removed and the top layer collected. To the top layer was added 100 mL ether and anhydrous magnesium sulfate and stirred overnight. The contents were then filtered with a celite pad. The ether solvent was then stripped off using a rotavapor and the residue was further stripped under high vacuum (0.025 mmHg) at about 80-90° C. for 5 hours to give the final purified product. SEC data showed Mn of 1375, Mw of 2980.

Example 3

Preparation of NVP Oligomer-terminated Fumarate Prepolymer of polydimethylsiloxane To a thoroughly dried 500-mL round bottom flask equipped with a reflux condenser was added bis-$\alpha,\omega$-hydroxybutyl polydimethylsiloxane (Mn 1376, 55.02 grams, 0.0399 mole) and fumaryl chloride (15.4 grams, 0.10 moles). The mixture was heated with an oil bath at about 70° C. under nitrogen blanket. After two hours, the reaction was complete and the contents of the flask (contents) was stripped under vacuum (5-6 mmHg) at about 80° C. for 2 hours.

The IR spectrum showed two kinds of peaks for carbonyl groups—both acid chloride and ester. To the contents was then added 16.64 g (0.04 mole) of the reactive NVP oligomer of Example 1 and 100 mL of methylene chloride. The content was heated under reflux until all acid chloride group was disappeared totally (by IR 1769 cm-1) (2 hours). Then the mixture was cooled. 5.41 grams of sodium bicarbonate was added to neutralize the content while stirring overnight.

Added 600 mL of methylene chloride. Then filtered the solution and extracted it with 100 mL of water. The organic layer was separated and the solvent was stripped to give a yellowish viscous fluid product.

Example 4

Preparation of Hydrogel Films Containing the Fumarate-containing Prepolymer and other Comonomers (UV Curing)

A monomer mix consisting of the prepolymer as described in Example 3, 35 parts (all parts by weight), 3-methacryloxypropyl tris(trimethylsiloxy)silane (TRIS), 35 parts, N,N-dimethylacrylamide (DMA) 30 parts, Hexanol, 40 parts and Darocur-1173, 0.3 parts was prepared. The mix was filtered through a 1.2 micron filter. The mix was then cast between two silane-treated glass plates and cured under UV for 2 hours. After extracting the released film in ethanol overnight, the dried films were saturated in buffered saline to give hydrogel films with water content of 41.3%, modulus 76.9 g/mm$^2$, elongation 59% and tear strength 3.0 g/mm.

Comparative Example 1

A comparable formulation derived from a fumarate-containing prepolymer end capped with t-butylamine and other components of the same weight ratio provided in Example 4 gave a hydrogel with a water content of 24% and a modulus of 97 g/mm2.

Example 5

Preparation of Reactive Oligomer Derived from N,N-dimethylacrylamide

To a thoroughly dried 1000-mL round bottom flask equipped with a reflux condenser, Nitrogen inlet, was charged N,N dimethylacrylamide (140.05 g), 2-mercaptoethanol (19.8 ml), 450 mL anhydrous tetrahydrofuran and Vazo-64 (1.8247 gram). The contents, while stirred at room temperature, were bubbled with nitrogen for about 15 minutes. The contents were then heated to reflux for 48 hours. IR indicated no vinyl groups present. The solution was then condensed to 120 mL and then poured into 1200 mL of ether to precipitate the product. The product was dissolved/precipitated twice. The final product was a gum. The molecular weight of the oligomer product was determined by acid-base titration. It was first allowed to react with an excess amount of phenyl isocyanate, then with excess amount of dibutylamine, both in THF, followed by titrating with standardized 0.1 N hydrochloric acid. The molecular weight as determined was 731. SEC: Mn=993, Mw=2673.

Example 6

Preparation of DMA Oligomer-terminated Fumarate Prepolymer of polydimethylsiloxane To a thoroughly dried 500-mL round bottom flask equipped with a reflux condenser was added bis-$\alpha,\omega$-hydroxybutyl polydimethylsiloxane (Mn 1388, 26.6 grams) and fumaryl chloride (2.86 grams). The mixture was heated with an oil bath at about 70-75° C. under nitrogen blanket. After two hours, the reaction was complete and the contents of the flask (contents) were stripped under vacuum (1-2 mmHg) at about 80° C. for 2 hours. The temperature was then lowered to about 50° C. and 27.75 g of the reactive DMA oligomer of Example 5 and 125 mL of methylene were added. The contents were heated under reflux until all acid chloride group disappeared totally (by IR 1769 cm-1). Then the mixture was cooled. Sodium bicarbonate was added to neutralize the contents while stirring overnight. 600 mL of methylene chloride was added to the neutralized contents. The solution was filtered and extracted with 100 mL of water. The organic layer was separated and the solvent was stripped to give a gummy solid product.

Example 7

Preparation of Hydrogel Films Using the Prepolymer of Example 6

A monomer mix containing the prepolymer of Example 6 (30 parts, all parts by weight) 3-methacryloxypropyl tris(trimethylsiloxy)silane (TRIS), (30 parts), N,N-dimethylacrylamide (DMA), (40 parts), Hexanol, (20 parts) and Darocur-1173, (0.5 parts), was prepared. The mix was then cast and processed into hydrogel films according to the procedure described in Example 4. The hydrogel had a water content of 61%. The hydrogel film was cloudy, Comparative Example 2

A comparable formulation derived from a fumarate-containing prepolymer end capped with t-butylamine, and other components of the same weight ratio as Example 7, gave a hydrogel with a water content of 35% and the films were clear.

Example 8

Preparation of Hydrogel Films Using the Prepolymer of Example 6

A monomer mix containing the prepolymer of Example 6, (15 parts, all parts by weight) a fumarate-containing prepolymer prepared with a polydimethylsiloxane of the same Mn as that of Example 2, but end capped with t-butylamine, (15 parts), 3-methacryloxypropyl tris(trimethylsiloxy)silane (TRIS), (30 parts), N,N-dimethylacrylamide (DMA), (40 parts), Hexanol, (20 parts) and Darocur-1173, (0.5 parts) was prepared. The mix was then cast and processed in hydrogel films according to the procedure described in Example 4. The hydrogel had a water content of 51%. The hydrogel film was hazy.

DISCUSSION

Comparative example 1 demonstrates that a polymer prepared according to the invention herein provides a hydrogel with improved water content and modulus. Comparative example 2 demonstrates that films prepared according to the invention herein have improved water content.

Contact lenses manufactured using the unique materials of the present invention are used as is customary in the field of opthalmology. While there is shown and described herein certain specific structures and compositions of the present invention, it will be manifest to those skilled in the art that various modifications may be made without departing from the spirit and scope of the underlying inventive concept and that the same is not limited to particular structures herein shown and described except insofar as indicated by the scope of the appended claims.

What is claimed is:

1. A copolymer prepared by polymerizing a monomer mixture comprising,
    (A) 10 to 80 weight % of at least one prepolymer selected from the group consisting of compounds having the following formula:

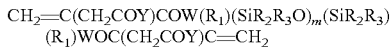

and

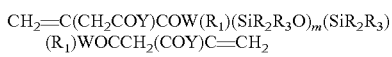

wherein $R_1$ is selected from the group consisting of alkylenes and alkylenes containing ether linkages, $R_2$ and $R_3$ are independently alkyl or phenyl groups, unsubstituted or substituted with halogen and ether linkages, W is O or NH, m is an integer between 2 and 200, and Y is a residue derived from a reactive oligomer of hydrophilic monomers, and
    (B) 10 to 90 weight % of at least one copolymerizable device-forming monomer.

2. The copolymer of claim 1 wherein the monomer mixture comprises:
    10 to 50 weight % of at least one additional silicone-containing monomer and 10 to 50 weight % of at least one copolymerizable device-forming hydrophilic monomer.

3. The copolymer of claim 1 wherein component (A) has the following formula:

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from hydrophilic monomers selected from the group consisting of amide, hydroxyl and zwitterionic containing hydrophilic monomers and is in a trans configuration.

4. The copolymer of claim 1 wherein component (A) has the following formula:

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from hydrophilic monomers selected from the group consisting of amide, hydroxyl and zwitterionic containing hydrophilic monomers and is in a cis configuration.

5. The copolymer of claim 1 wherein component (A) has the following formula:

$$CH_2=C(CH_2COY)COW(R_1)(SiR_2R_3O)_m(SiR_2R_3)$$
$$(R_1)WOC(CH_2COY)C=CH_2$$

or $$CH_2=C(CH_2COY)COW(R_1)(SiR_2R_3O)_m(SiR_2R_3)$$
$$(R_1)WOCCH_2(COY)C=CH_2$$

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from hydrophilic monomers selected from the group consisting of amide, hydroxyl and zwitterionic containing hydrophilic monomers.

6. The copolymer of claim 1 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer and is in a trans configuration.

7. The copolymer of claim 1 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer and is in a cis configuration.

8. The copolymer of claim 1 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from an ethylenically unsaturated lactam containing monomer.

9. The copolymer of claim 1 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone and is in a trans configuration.

10. The copolymer of claim 1 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 100, W is O and Y a residue derived from a reactive oligomer derived from N-vinylpyrrolidone and is in a cis configuration.

11. The copolymer of claim 1 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone.

12. The copolymer of claim 2 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from hydrophilic monomers selected from the group consisting of amide, hydroxyl and zwitterionic containing hydrophilic monomers and is in a trans configuration.

13. The copolymer of claim 2 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from hydrophilic monomers selected from the group consisting of amide, hydroxyl and zwitterionic containing hydrophilic monomers and is in a cis configuration.

14. The copolymer of claim 2 wherein component (A) has the following formula:

$$CH_2=C(CH_2COY)COW(R_1)(SiR_2R_3O)_m(SiR_2R_3)(R_1)WOC(CH_2COY)C=CH_2$$

or $$CH_2=C(CH_2COY)COW(R_1)(SiR_2R_3O)_m(SiR_2R_3)(R_1)WOC(CH_2COY)C=CH_2$$

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from hydrophilic monomers selected from the group consisting of amide, hydroxyl and zwitterionic containing hydrophilic monomers.

15. The copolymer of claim 2 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer and is in a trans configuration.

16. The copolymer of claim 2 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer and is in a cis configuration.

17. The copolymer of claim 2 wherein component (A) has the following formula:

$$CH_2=C(CH_2COY)COW(R_1)(SiR_2R_3O)_m(SiR_2R_3)(R_1)WOC(CH_2COY)C=CH_2$$

or $$CH_2=C(CH_2COY)COW(R_1)(SiR_2R_3O)_m(SiR_2R_3)(R_1)WOC(CH_2COY)C=CH_2$$

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from an ethylenically unsaturated lactam containing monomer.

18. The copolymer of claim 2 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone and is in a trans configuration.

19. The copolymer of claim 2 wherein component (A) has the following formula:

$$YOC-CH=CHCOW(R_1)(SiR_2R_3O)_m(SiR_2R_3)(R_1)WOCCH=CH-COY$$

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone and is in a cis configuration.

20. The copolymer of claim 2 wherein component (A) has the following formula:

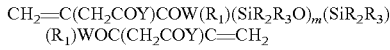

or

wherein $R_1$ is selected from the group consisting of alkylenes and alkylenes containing ether linkages, $R_2$ and $R_3$ are methyl, m is an integer between 5 and 200, W is O and Y is a residue derived from a reactive oligomer derived from N-vinylpyrrolidone.

21. A medical device comprising a copolymer prepared by polymerizing a monomer mixture comprising, as main components, (A) 10 to 90 weight % of at least one prepolymer selected from the group consisting of compounds having the following formula:

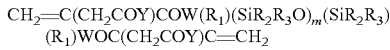

and

wherein $R_1$ is selected from the group consisting of alkylenes and alkylenes containing ether linkages, $R_2$ and $R_3$ are independently alkyl or phenyl groups, unsubstituted or substituted with halogen and ether linkages, W is O or NH, m is an integer between 2 and 200, and Y is a residue derived from a reactive oligomer of hydrophilic monomers, and (B) 10 to 90 weight % of at least one copolymerizable device-forming monomer.

22. The medical device of claim 21 wherein the monomer mixture comprises:

10 to 50 weight % of at least one additional silicone-containing monomer hydrophilic monomer and 10 to 50 weight % of at least one copolymerizable device-forming hydrophilic monomer.

23. The medical device of claim 21 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from hydrophilic monomers selected from the group consisting of amide, hydroxyl and zwitterionic containing hydrophilic monomers and is in a trans configuration.

24. The medical device of claim 21 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from hydrophilic monomers selected from the group consisting of amide, hydroxyl and zwitterionic containing hydrophilic monomers and is in a cis configuration.

25. The medical device of claim 21 wherein component (A) has the following formula:

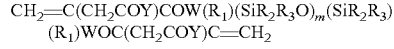

or

wherein $R_1$ is selected from the group consisting of alkylenes and alkylenes containing ether linkages, $R_2$ and $R_3$ are methyl, m is an integer between 5 and 100, W is O and Y is a reactive oligomer derived from hydrophilic monomers selected from the group consisting of amide, hydroxyl and zwitterionic containing hydrophilic monomers.

26. The medical device of claim 21 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer and is in a trans configuration.

27. The medical device of claim 21 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer and is in a cis configuration.

28. The medical device of claim 21 wherein component (A) has the following formula:

or

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer.

29. The medical device of claim 21 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone and is in a trans configuration.

30. The medical device of claim 21 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone and is in a cis configuration.

31. The medical device of claim 21 wherein component (A) has the following formula:

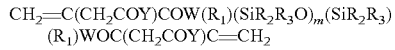

or

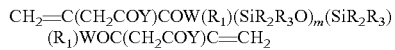

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone.

32. The medical device of claim 22 wherein component (A) has the following formula:

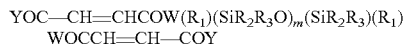

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from hydrophilic monomers selected from the group consisting of amide, hydroxyl and zwitterionic containing hydrophilic monomers and is in a trans configuration.

33. The medical device of claim 22 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from hydrophilic monomers selected from the group consisting of amide, hydroxyl and zwitterionic containing hydrophilic monomers and is in a cis configuration.

34. The medical device of claim 22 wherein component (A) has the following formula:

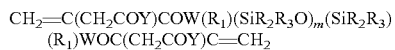

or

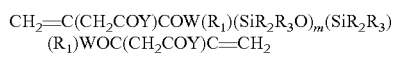

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from hydrophilic monomers selected from the group consisting of amide, hydroxyl and zwitterionic containing hydrophilic monomers.

35. The medical device of claim 22 wherein component (A) has the following formula:

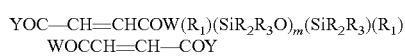

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer and is in a trans configuration.

36. The medical device of claim 22 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer and is in a cis configuration.

37. The medical device of claim 22 wherein component (A) has the following formula:

or

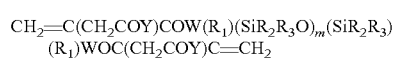

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from an ethylenically unsaturated lactam containing monomer.

38. The medical device of claim 22 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone and is in a trans configuration.

39. The medical device of claim 22 wherein component (A) has the following formula:

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone and is in a cis configuration.

40. The medical device of claim 22 wherein component (A) has the following formula:

or

wherein $R_1$ is selected from the group consisting of alkylenes and alkylenes containing ether linkages, $R_2$ and $R_3$ are methyl, m is an integer between 5 and 100, W is O and Y is a residue derived from a reactive oligomer derived from N-vinylpyrrolidone.

41. The medical device of claim 21 wherein the medical device is selected from the group consisting of heart valves, controlled drug delivery systems intraocular lenses, contact lenses, intrauterine devices, vessel substitutes, artificial ureters and artificial breast tissue.

42. The medical device of claim 41 wherein the medical device is a contact lens.

43. The medical device of claim 42 wherein the medical device is a soft contact lens.

44. The medical device of claim 22 wherein the medical device is selected from the group consisting of heart valves, controlled drug delivery systems, intraocular lenses, contact lenses, intrauterine devices, vessel substitutes, artificial ureters and artificial breast tissue.

45. The medical device of claim 44 wherein the medical device is a contact lens.

46. The medical device of claim 45 wherein the medical device is a soft contact lens.

* * * * *